United States Patent [19]

Clark et al.

[11] Patent Number: 5,114,233

[45] Date of Patent: May 19, 1992

[54] METHOD FOR INSPECTING ETCHED WORKPIECES

[75] Inventors: Linda A. Clark, Mountainside; Richard A. Gottscho; Joseph B. Kruskal, both of Maplewood; Diane Lambert, Berkeley Heights, all of N.J.

[73] Assignee: AT&T Bell Laboratories, Murray Hill, N.J.

[21] Appl. No.: 594,774

[22] Filed: Oct. 9, 1990

[51] Int. Cl.⁵ .................................................. G01B 9/02
[52] U.S. Cl. ...................................... 356/354; 356/355; 356/384
[58] Field of Search ................ 356/354, 355, 356, 384; 156/626

[56] References Cited

U.S. PATENT DOCUMENTS

| | | | |
|---|---|---|---|
| 4,039,370 | 8/1977 | Kleinknecht | 156/626 |
| 4,141,780 | 2/1979 | Kleinknecht | 156/626 |
| 4,155,098 | 5/1979 | Roach et al. | 356/355 |
| 4,180,830 | 12/1979 | Roach | 356/355 |
| 4,303,341 | 12/1981 | Kleinknecht | 356/384 |
| 4,330,213 | 5/1982 | Kleinknecht | 356/355 |
| 4,408,884 | 10/1983 | Kleinknecht | 356/355 |

OTHER PUBLICATIONS

T. F. Chan, "An Improved Algorithm for Computing the Singular Value Decomposition," ACM Transactions on Mathematical Software, vol. 8, No. 1, pp. 72-83 (1982).

G. H. Golub and C. Reinsch, "Singular Value Decomposition and Least Squares Solutions," Numerische Mathematik 14, pp. 403-420 (1970).

L. Kaufman, "Application of Dense Householder Transformations to a Sparse Matrix," ACM Transactions on Mathematical Software, vol. 5, No. 4, pp. 442-450 (1979).

Primary Examiner—Samuel A. Turner
Attorney, Agent, or Firm—Glen E. Books

[57] ABSTRACT

The present invention is predicted upon the discovery by applicants that is scattered light from an etched workpiece is measured over many orders of diffraction, important characteristics of the etched workpiece can be correlated with the principal component content of the intensity characteristic. In accordance with the present invention, an etched workpiece is inspected by 1) exposing the workpiece to a beam of coherent light, 2) measuring the intensity of the light scattered from the workpiece over a range of spatial frequencies corresponding to a plurality of diffraction orders, 3) determining the principal component content of the tested workpiece intensity envelope, and 4) accepting or rejecting the workpiece in accordance with whether or not the principal component content satisfies predetermined criteria. In preferred embodiments the principal components are determined in relation to a plurality of reference measurements by singular value decomposition.

5 Claims, 4 Drawing Sheets

METHOD FOR INSPECTING ETCHED WORKPIECES

BACKGROUND OF THE INVENTION

The present invention relates to optical inspection of workpieces and, in particular, to a method for inspecting etched semiconductor workpieces using the principal components of scattered light intensity to distinguish differences in the nature of etched lines, including differences in profile, depth, slope and linewidth.

It is common and necessary practice in the manufacture of integrated circuits to periodically inspect etched wafer workpieces for changes in critical line width, line profile and etched depths. Previously such inspections could be performed rapidly and non-destructively by a technician using an optical microscope. But as semiconductor technology has evolved to micron and submicron line widths, inspection by optical microscopy is no longer adequate. With today's submicron patterns, inspection typically involves selecting a sample of wafers from a processing lot, cleaving the wafers and inspecting the cleaved wafers with a scanning electron microscope. This approach is time-consuming, destructive and limited to a small subset of the wafer lot.

In an effort to replace this time-consuming and destructive testing process, a variety of experimental efforts have been directed toward the development of inspection and monitoring methods based upon the scattering of a beam of light directed onto the workpiece surface. Such techniques have typically utilized only a narrow range of scattering angles, typically the specular intensity and the first order. While promising experimental results have been reported, these techniques have not demonstrated the ability to discriminate between submicron variations in etching depth and variations in etching profile.

SUMMARY OF THE INVENTION

The present invention is predicated upon the discovery by applicants that if scattered light from an etched workpiece is measured over a range of spatial frequencies encompassing plural orders of diffraction, important characteristics of the etched workpiece can be correlated with the principal component content of the intensity characteristic. In accordance with the invention, an etched workpiece is inspected by 1) exposing the workpiece to a beam of coherent light, 2) measuring the intensity of the light scattered from the workpiece over a range of spatial frequencies corresponding to a plurality of diffraction orders, 3) computing the principal component coordinates of the intensity envelope, and 4) accepting or rejecting the workpiece in accordance with whether or not the principal component coordinates satisfy predetermined criteria. In a preferred embodiment the principal components are determined in relation to a plurality of reference measurements by computing the singular value decomposition.

BRIEF DESCRIPTION OF THE DRAWING

The advantages, nature and various additional features of the invention will appear more fully upon consideration of the illustrative embodiments now to be described in detail in connection with the accompanying drawings in which.

DETAILED DESCRIPTION

This invention is predicated upon applicant's discovery that if scattered light from a workpiece is measured over a range of spatial frequencies encompassing plural orders of diffraction, important characteristics of the workpiece can be correlated with the coordinates with respect to the principal components of the intensity envelope. This discovery permits rapid, non-destructive testing of workpieces, such as etched semiconductor workpieces, by measurement of their light scattering intensity envelopes and determination of the coordinates with respect to the principal components of those envelopes.

The inventive method of inspection may be best explained in two steps: first, a preliminary step of computing the principal components; and, second, the method of inspecting a workpiece using the coordinates with respect to principal components.

Figure 1:
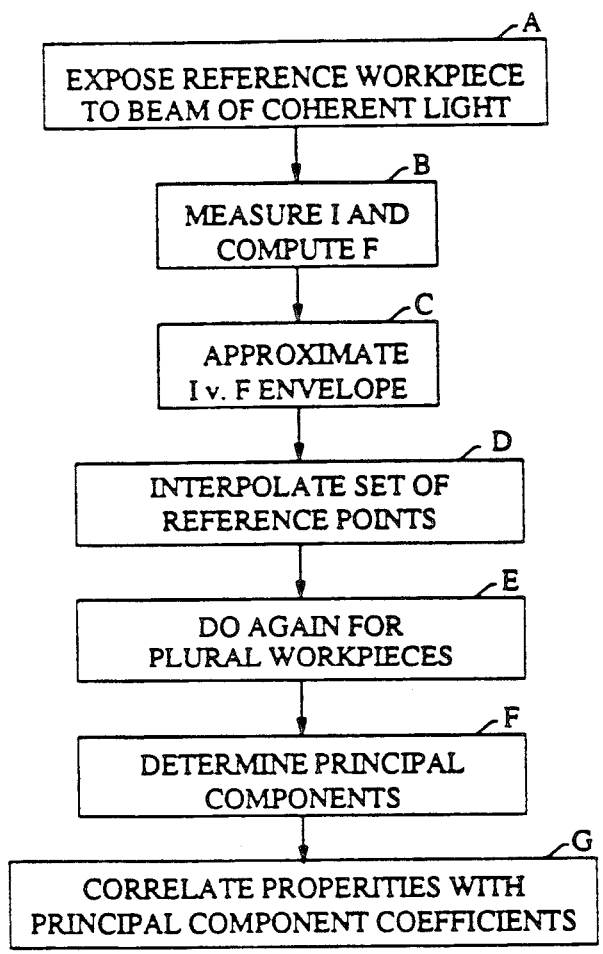
FIG. 1 is a block diagram illustrating a preferred method for determining a set of principal components for use in practicing the inventive method of inspection.

As shown in FIG. 1, a preliminary step to inspection in accordance with the invention is 1) the computation of one or more principal components from reference workpieces of the type to be inspected and 2) correlation of the workpiece characteristics to be inspected with the values of the coordinates with respect to the principal components. While simple cases permit theoretical calculation of principal components, most practical applications require a preliminary step which involves measuring the light scattering characteristics of workpieces having known characteristics.

As shown in FIG. 1A, the first step in the preliminary process is to select a workpiece of known characteristics, e.g., etching characteristics that are overcut, undercut, or straight profile, and to expose the workpiece to a beam of coherent light. The next step, shown in FIG. 1B, is to measure the intensity of the light scattered from the workpiece over plural orders of diffraction and to compute the spatial frequency F for each such intensity measurement.

Figure 2:
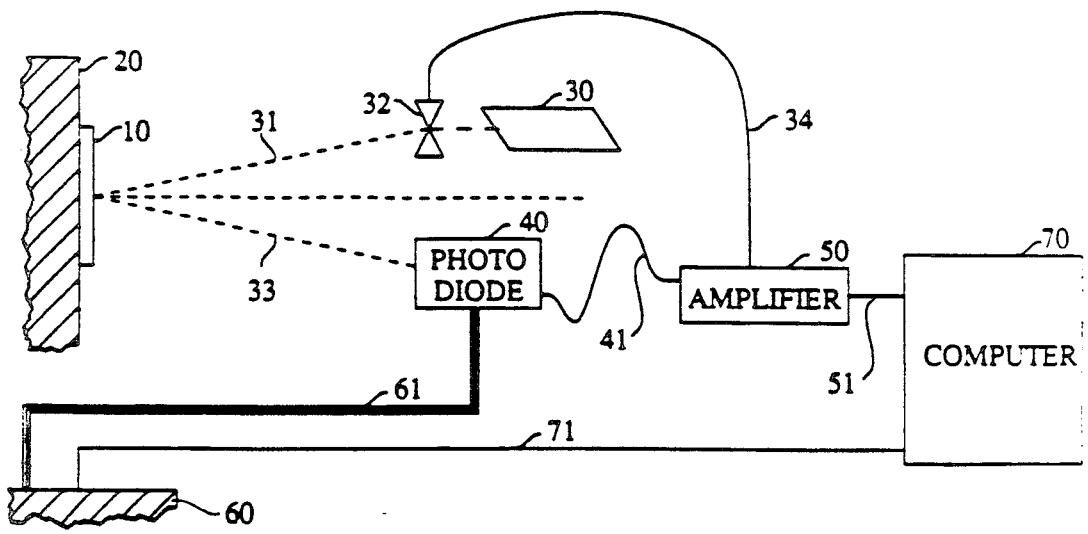
FIG. 2 is a schematic cross-section of typical apparatus for measuring scattered light intensity as a function of spatial frequency.

Apparatus for making the desired measurements and computations is schematically shown in FIG. 2. In essence, a reference workpiece 10 of known characteristics (e.g. known etching profile) is disposed on a support 20 which is preferably tiltable. A laser 30 is mounted and oriented for directing a beam of coherent light 31 onto the workpiece, and a photodiode 40 is movably mounted and oriented for receiving light 33 scattered from the workpiece. The output of photodiode 40 is an electrical signal representative of the scattered light intensity. This output is preferably applied via leads 41 to one terminal of a phase sensitive amplifier 50. The light from laser 30 is preferably passed through a chopper 32, and an electrical signal from the chopper indicative of the periods when laser light is passing through the chopper is applied via leads 34 to a second terminal of phase sensitive amplifier 50. With this arrangement, the output of amplifier 50 is an electrical signal indicative of the intensity of the light received by photodiode 40 only when the laser beam is passing through the chopper. Thus the effects of ordinary ambient lighting can be ignored. This output is presented to a computer 70 via leads 51.

The photodiode 40 is preferably mounted on the rotating arm 61 of a rotational stage 60 with the axis of rotation aligned with the target area on the workpiece. This stage can be controlled by a computer 70 via leads 71 so that the computer controls the angular displacement of the photodiode.

An exemplary arrangement of the apparatus of FIG. 2 employed a Melles Griot helium neon laser for laser 30, a Laser Precision chopper 32 and a Centronic OS-DI-5B photodiode 40 with a 5 mm, bugeye lens. The photodiode was mounted on a Newport Research Corp., Model 495 Optically Encoded Rotational Stage equipped with a Newport Model 855C Controller. Amplifier 50 was a Princeton Applied Research Model HR-8 phase sensitive amplifier.

The computer 70 is programmed a) to measure and record the scattered light intensity over a wide range of angles, b) to calculate and record the spatial frequency F at each measurement, c) to determine an envelope function for the intensity versus frequency curve, and d) after the measurement of a plurality of samples, to determine one or more principal components of the intensity envelopes.

In practice, the angle of incidence $\theta_i$ of beam 31, typically about 90°, and the wavelength $\lambda$ of laser 30, typically about 0.6328 micrometers, are entered into the computer. The location of photodiode 40 is conveniently initialized at spatial frequency zero by placing the diode in the specularly reflected beam. Under computer control, arm 61 is then rotated over an angular range between about 90° and 180° while several hundred intensity measurements are made and recorded. Preferably the range of spatial frequencies exceeds about one inverse micrometer encompassing more than 30 local maxima. Along with each intensity, I, the computer records the corresponding spatial frequency F calculated in accordance with the relation $$F = \frac{\sin\theta_s - \sin\theta_i}{\lambda}$$

where $\theta_s$ is the angle of the scattered light with respect to the workpiece normal, $\theta_i$ is the incident angle, and $\lambda$ is the wavelength in micrometers. F is given in inverse micrometers.

Figure 4A:
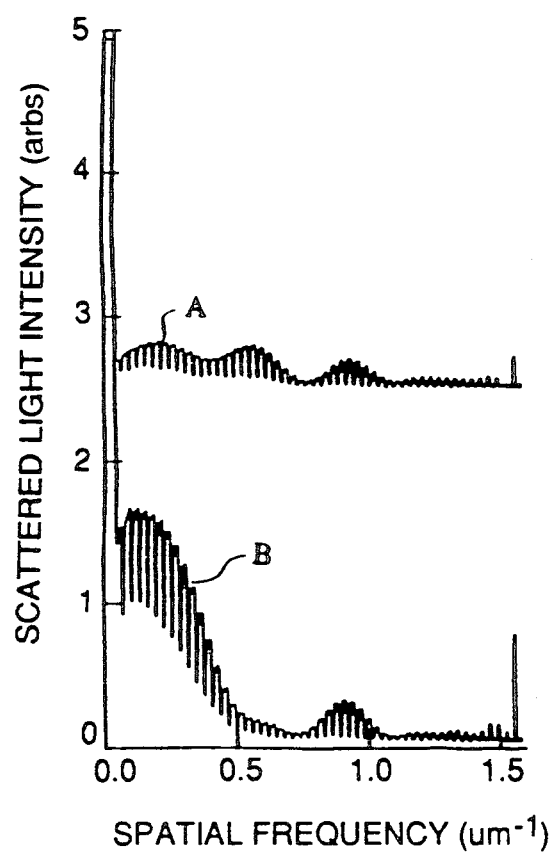
FIGS. 4a, b and 5a, b are graphical illustrations, useful in understanding the invention, showing the scattered light intensity as a function of spatial frequency for various reference workpieces.
Figure 4B:
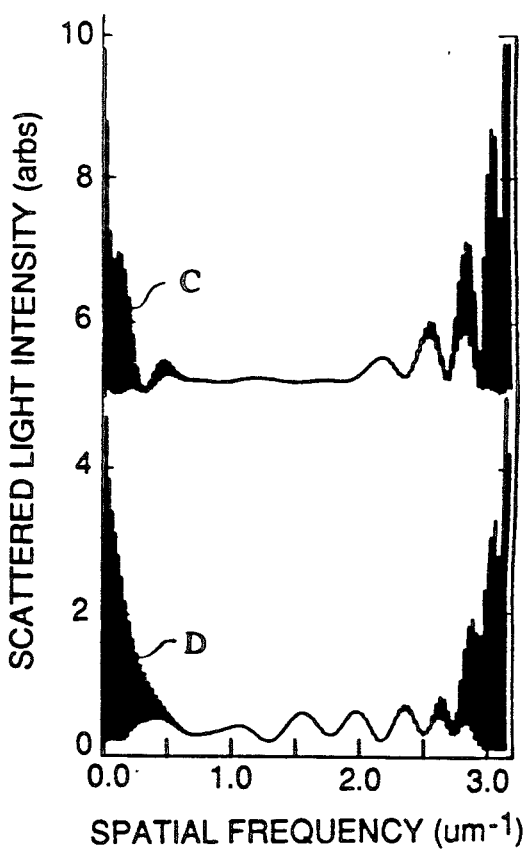
Figure 5A:
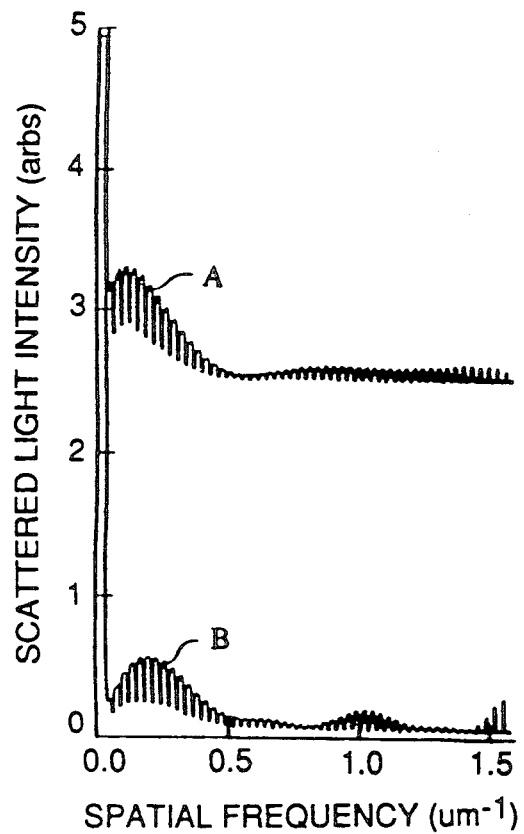
Figure 5B:
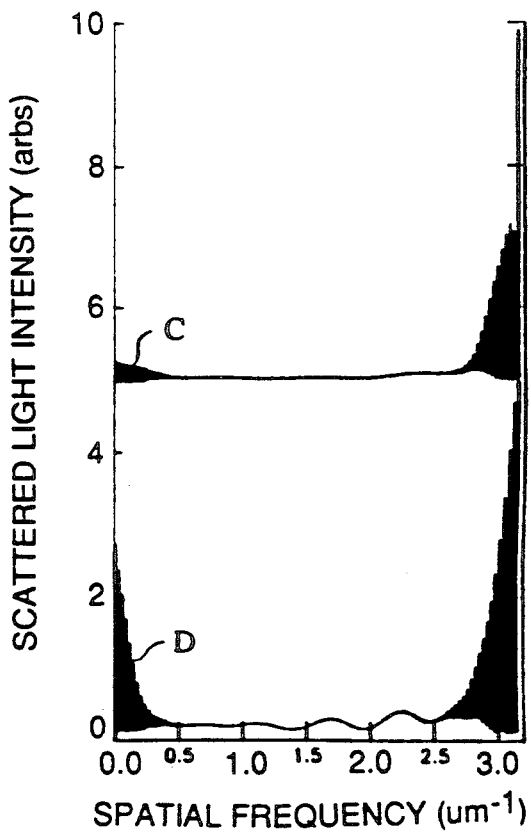

FIGS. 4 and 5 show typical scattered light versus spatial frequency curves for a variety of workpieces. Specifically, the figures show the scattered light intensities for etched silicon test grids of 1.5 micrometer lines having spacing of 32 micrometers. Intensities were measured for both a normal incidence beam and for a grazing incidence beam. In FIG. 4, curve A, the beam incidence was normal and the grid had lines with a vertical profile. Curve C is for the same grid but with a grazing incidence beam. Curve B is with beam incidence normal on a grid having lines which are "overcut". Curve D is the same grid with the beam incidence at a grazing angle.

In FIG. 5, curve A shows the intensity characteristic for a normal incidence on vertical profile grid of shallow etch depth. Curve C shows the result of a grazing incidence beam on the same grid. Curve B shows the characteristic for normal incidence on a grid of vertical profile with greater etching depth. Curve D shows the result of a grazing incidence beam on the same grid.

The next step in the preferred preliminary process, as shown as FIG. 1C, is to approximate the envelope of the intensity versus spatial frequency function thus measured. A preferred approach is as follows: First the function $S_1$, of roughly 500 measured intensity versus frequency pairs, $S_1 = [[I_1, F_1] [I_2, F_2] \ldots, (I_{500}, F_{500})]$ is transformed into an envelope function $S_2$ by determining which of the points (I, F) correspond to local intensity maxima $(I_m, F_m)$. An appropriate criterion is to choose as a local maximum each (I,F) pair wherein I is greater than or equal to the intensity values in the four pairs on either side of (I,F). This process leads to an envelope function of about 50 pairs, i.e. $S_2 = [(I_{m1}, F_{m1}), (I_{m2}, F_{m2}), \ldots, (I_{m50}, F_{m50})]$. The specular maximum at and near the zero order is omitted from $S_2$.

Since the frequencies in $S_2$ are not spaced the same from one reference workpiece to another, advantageously the next step shown in FIG. 1D is to generate an interpolated envelope function $S_3$ consisting of about 40 pairs having intensity values $S_3 = (I_1, I_2, \ldots, I_{40})$ linearly interpolated for a fixed set of frequencies ($F_1, F_2, \ldots, F_{40}$).

As shown in FIG. 1E, the next step is to repeat the above-described process for a plurality of N measurements of regions having known characteristics. Applicants used 35 reference measurements from eight workpieces in their experiments. The result of this process is a plurality of interpolated envelope functions, where the nth envelope is $(I_{n1}, I_{n2}, \ldots, I_{n40})$, which can be represented as a N by 40 matrix.

The next step in the preferred preliminary process is to determine one or more principal components of this matrix. This determination can be made by a computer in two steps. The first step is to substract from each element in each column the mean value of elements in that respective column. This is referred to as centering the matrix, and the rows are now "centered" interpolated envelopes. The second step is to apply to the centered matrix, the singular value decomposition algorithm. For a detailed explanation of the singular value decomposition algorithm and its operation, see:

1. T. F. Chan, "An Improved Algorithm for Computing the Singular Value Decomposition," *ACM Transactions on Mathematical Software*, Vol. 8, No. 1, pp. 72-83 (1982).

2. G. H. Golub and C. Reinsch, "Singular Value Decomposition and Least Squares Solutions," *Numerische Mathematik* 14, pp. 403-420 (1970).

3. L. Kaufman, "Application of Dense Householder Transformations to a Sparse Matrix," *ACM Transactions on Mathematical Software*, Vol. 5, No. 4, pp. 442-450 (1979). The result of the process is a new N by 40 matrix whose rows are the principal components ($P_1, P_2, \ldots, P_n$) which in various linear combinations can best approximate the centered interpolated envelopes of all reference measusrments.

The final step in the preferred preliminary process is to correlate the known properties of the reference measurements and the coordinates of the envelopes with respect to one or more principal components. Applicants determined that useful correlations concerning etching characteristics could be made by analyzing the centered, interpolated envelope function with respect to the first two principal components. In other words, if, for a given workpiece, the centered interpolated envelope function is approximated by the linear combination $E \approx C_1P_1 + C_2P_2$, where $C_1$ and $C_2$ are constants referred to as coordinates, then $C_1$ and $C_2$ provide useful information concerning the etching characteristics of the workpiece.

Figure 6:
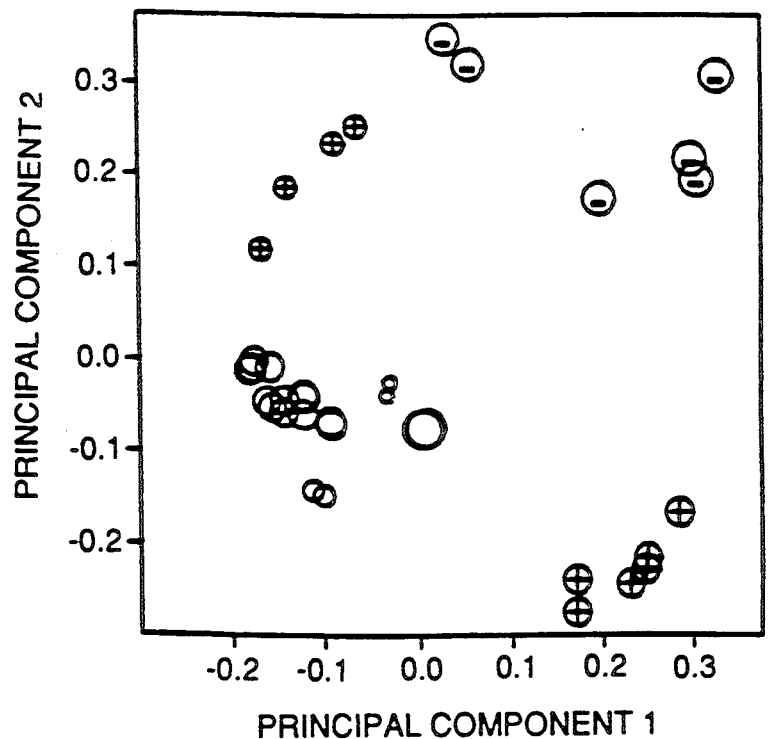
FIG. 6 is a graphical illustration, useful in understanding the invention, plotting the coordinates with respect to the first and second principal components from intensity envelopes of 35 reference measurements.

An example of this correlation is shown in FIG. 6 which plots $[C_1, C_2]$ for a run of 35 reference measurements with grids as described above. The area of the circles is proportional to known etch depth (with maximum depth of 2.8 micrometers), undercut etch profiles are denoted by a minus sign within the circle, overcut etch profiles are denoted by a plus sign within the circle, and vertical etch profiles are denoted by empty circles. As can be seen, the correlation represented by the clustering of profiles with like characteristics, permits well-defined criteria for inspection. The vertical profiles are bounded by $C_1 = [-0.2, -0.10]$ and $C_2 = [-0.1, 0.0]$. The overcut profiles are bounded by $C_1 = [0.15, 0.30]$ and $C_2 = [-0.3, 0.15]$. Simpler or more complex regions could be used as inspection criteria.

Figure 3:
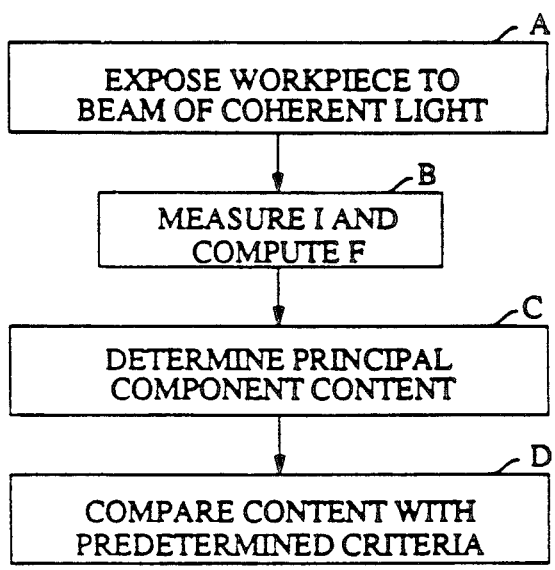
FIG. 3 is a block diagram illustrating the steps involved in inspecting a workpiece in accordance with a preferred embodiment of the invention.

With this preliminary process completed, the method for rapid and nondestructive testing of workpieces may be easily described in relation to FIG. 3. First, as shown in FIG. 3A, the workpiece to be inspected is exposed to a beam of light in the manner described in connection with FIG. 2, and, as shown in FIG. 3B, the scattered intensity, I, is then measured and recorded along with the calculated spatial frequency, F, as described above.

The next step in the inspection process shown in FIG. 3C is to determine the coordinates of the centered interpolated intensity envelope with respect to one or more principal components, e.g., $P_1$ and $P_2$. The centered interpolated envelope function is generated in the same fashion as described above, and $C_1$ and $C_2$ are determined, such that $C_1P_1 + C_2P_2$ the best least squares approximation to the envelope function. This determination is made in accordance with a linear regression algorithm or in accordance with other techniques well known in the art.

The final step in the inspection process shown in FIG. 3D, is to accept or reject the workpiece in accordance with whether or not the coordinates meet predetermined criteria, e.g. whether or not $(C_1, C_2)$ falls within a predetermined region, such as a rectangular region. Thus workpieces of the type represented in FIG. 6 would pass if $C_1 = [-0.2, -0.10]$, $C_2 = [-0.1, 0.0]$ corresponding to a vertical profile and fail if $C_1 = [0.15, 0.30]$, $C_2 = [-0.3, 0.15]$ corresponding to an overcut profile.

It is to be understood that the above described embodiments are illustrative of only a few of the many possible specific embodiments which can represent applications of the principles of the invention. Numerous and varied other arrangements can be readily devised by those skilled in the art from these principles without departing from the spirit and scope of the invention.

We claim:

1. A method for optically inspecting workpieces comprising the steps of:
    determining by singular value decomposition a set of principal components for the intensity envelope of light scattered from one or more reference workpieces over a range of spatial frequencies corresponding to a plurality of diffraction orders,
    defining criteria for the acceptability or nonacceptability of a workpiece in accordance with the principal component content of the intensity envelope of the workpiece;
    exposing a workpiece to be tested to a beam of coherent light;
    measuring the intensity of the light scattered from said workpiece over a range of spatial frequencies corresponding to a plurality of diffraction orders,
    determining the principal component content of the intensity envelope of said workpiece to be tested for one or more principal components; and
    accepting or rejecting said workpiece in accordance with whether or not said principal component content satisfies said criteria.

2. The method according to claim 1 wherein the principal component content of the intensity envelope of said workpiece to be tested is determined by ascertaining the coefficients of said envelope with respect to one or more principal components.

3. The method according to claim 2 wherein said principal component content of said intensity envelope is determined by ascertaining the coefficients of said envelope with respect to the first two principal components.

4. The method of claims 1, 2, or 3 wherein said workpiece is an etched semiconductor workpiece.

5. The method of claims 1, 2, or 3 wherein said workpiece is an etched semiconductor workpiece containing a test grid of etched lines and said step of exposing said workpiece comprises directing a beam of coherent light onto said test grid.

* * * * *